United States Patent [19]

Purchio et al.

[11] Patent Number: 5,444,164
[45] Date of Patent: Aug. 22, 1995

[54] TGF-$\beta$ INDUCED GENE

[75] Inventors: Anthony F. Purchio; John E. Skonier; Michael G. Neubauer, all of Seattle, Wash.

[73] Assignee: Bristol-Myers Squibb Company, New York, N.Y.

[21] Appl. No.: 878,960

[22] Filed: May 4, 1992

Related U.S. Application Data

[63] Continuation-in-part of Ser. No. 833,835, Feb. 5, 1992, abandoned.

[51] Int. Cl.$^6$ ............................................. C07H 15/12
[52] U.S. Cl. .................. 536/23.5; 435/69.1; 530/399
[58] Field of Search ...................... 536/23.5; 530/399; 435/69.1

[56] References Cited

PUBLICATIONS

Inge et al. *J. of Immunology* 148:3847–56 (1992).
Keski-Oja et al. *J. of Cell Biol* 106:451–459 (1988).
Skouteris et al. *Biochem J.* 281:729–733 (1992).
Brunner, A. et al. (1991) Dialog Information Services, File 5: Biosis 1969 to the present, Accession No. 8563529 and "Identification of a gene family regulated by transforming growth factor-beta," DNA Cell Biology 10(4), 293–300.
Kallin, B. et al. (1991) "Cloning of a growth arrest-specific and transforming growth factor-beta-regulated gene, TI 1, from an epithelial cell line," Mol. and Cell Biol. 11(10), 5338–5345.
Pearson, C. A. et al. (1988) "Tenascin: cDNA cloning and induction by TGF-beta," EMBO J. 7(10), 2977–2981.
Assoian, R. K., A. Komoriya, C. A. Meyers, D. M. Miller and M. B. Sporn, (1983) Transformnig Growth Factor-$\beta$ in Human Platelets, J. Biol. Chem. 258:7155–7160.
Coffey, R. J., N. J. Sipes, C. C. Bascom, R. Graves--Deal, Claire Y. Penningrton, B. E. Weissman and H. L. Moses, (1988) Growth Modulation of Mouse Keratinocytes by Transforming Growth Factors, Cancer Res. 48:1596–1602.
Derynck, R. J. A. Jarrett, E. Y. Chen, D. H. Eaton, J. R. Bell, R. K. Assoian, A. B. Roberts, M. B. Sporn and D. V. Goeddel, (1985) Human transforming growth factor-$\beta$ complementary DNA sequence and expression in normal and transformed cells, Nature 316:701–705.
Derynck, R., J. A. Jarrett, E. Y. Chen, and D. V. Goeddel, (1986) The Murine Transforming Growth Factor-$\beta$ Precursor, J. Biol. Chem. 261:4377–4379.
Ignotz, R. A. and J. Massague, (1986) Transforming Growth Factor-$\beta$ Stimulates the Expression of Fibronectin and Collagen and Their Incorporation into the Extracellular Matrix, J. Biol. Chem. 261:4337–4345.
Loef, E. B., J. A. Proper, A. S. Goustin, G. D. Shipley, P. E. DiCoreto and H. L. Moses, (1986) Induction of c-sis mRNA and activity similar to platelet-derived growth factor by transforming growth factor $\beta$: A proposed model for indirect mitogenesis involving autocrine activity, Proc. Natl. Acad. Sci. USA 83:1453–1458.
Penttinen, R. P., S. Kobayashi and P. Bornstein, (1988) Transforming growth factor $\beta$ increases mRNA for matrix protein both in the presence and in the absence of changes in mRNA stability, Proc. Natl. Acad. Sci. USA 85:1105–1110.

(List continued on next page.)

Primary Examiner—Garnette D. Draper
Assistant Examiner—Shelly Guest Cermak
Attorney, Agent, or Firm—Joseph M. Sorrentino

[57] ABSTRACT

A new TGF-$\beta$ induced gene and protein is described. Treatment of TGF-$\beta$ growth arrested cells induces the production of a novel gene which encodes a 683 amino acid protein, designated BIG-H3, that contains four homologous repeat regions and which may represent a cell surface recognition molecule. This gene and protein is induced in mammalian cells, and specifically human cells, upon treatment with TGF-$\beta$, and is shown to inhibit the growth of tumor cells.

4 Claims, 12 Drawing Sheets

OTHER PUBLICATIONS

Pertovaara, L., L. Sistonen, T. J. Bos, P. K. Vogt, J. Keski-Oja and K. Alitalo, (1989) Enhanced *jun* Gene Expression Is an Early Genomic Response to Transforming Growth Factor β Stimulation, Molecular and Cellular Biology 9:1255-1264.

Ranchalis, J. E., L. E. Gentry, Y. Agawa, S. M. Seyedin, J. McPherson, A. Purchio and D. R. Twardzik, (1987) Bone-Derived and Recombinant Transforming Growth Factor β's are Potent Inhibitors of Tumor Cell Growth, Biochem. Biophys. Res. Commun. 148:783-789.

Skonier, J., M. Neubauer, L. Madisen, K. Bennett, G. D. Plowman and A. F. Purchio, (1992) cDNA Cloning and Sequence Analysis of βig-h3, a Novel Gene Induced in a Human Adenocarcinoma Cell Line after Treatment with Transforming Growth Factor-β, DNA and Cell Biology 11:511-522.

Tucker, R. F., G. D. Shipley, H. L. Moses and R. W. Holley (1984) Growth Inhibitor from BSC-1 Cells Closely Related to Platelet Type β Transforming Growth Factor, Science 226:705-707.

Zimm, K., L. McAllister and C. S. Goodman, (1988) Sequence Analysis and Neuronal of Fasciclin I in Grasshopper and Drosophila, Cell 53:577-583.

```
-47 GCTTGCCCGTCGGTCGCTAGCTCGCTCGGTGCGGGTCGTCCGCTCC                                                              -1
             ▼                      10                      ▼                  20
    Met Ala Leu Phe Val Arg Leu Leu Ala Leu Ala Leu Ala Thr Leu Ala Gly Pro Ala Ala Gly Pro
    ATG GCG CTC TTC GTG CGG CTC CTG GCT CTC GCC CTG GCT CTG GCC CTG GCG ACC CTG GCG GGT CCC                    75
                                35                                       45
    Ala Lys Ser Pro Tyr Gln Leu Val Leu Gln His Ser Arg Leu Arg Gly Arg Gln His Gly Pro Asn Val Cys Ala
    GCC AAG TCG CCC TAC CAG CTG GTG CTG CAG CAC AGC AGG CTC CGG GGC CGC CAG CAC GGC CCC AAC GTG TGT GCT       150
                        60                                          70
    Val Gln Lys Val Ile Gly Thr Asn Arg Lys Tyr Phe Thr Asn Cys Lys Gln Trp Tyr Gln Arg Lys Ile Cys Gly
    GTG CAG AAG GTT ATT GGC ACT AAT AGG AAG TAC TTC ACC AAC TGC AAG CAG TGG TAC CAA AGG AAA ATC TGT GGC       225
                        85                                          95
    Lys Ser Thr Val Ile Ser Tyr Glu Cys Cys Pro Gly Tyr Glu Lys Val Pro Gly Glu Lys Gly Cys Pro Ala Ala
    AAA TCA ACA GTC ATC AGC TAC GAG TGC TGT CCT GGA TAT GAA AAG GTC CCT GGG GAG AAG GGC TGT CCA GCA GCC       300
                        110                                     120
    Leu Pro Leu Ser Asn Leu Tyr Glu Thr Leu Gly Val Val Gly Ser Thr Thr Thr Gln Leu Tyr Thr Asp Arg Thr
    CTA CCA CTC TCA AAC CTT TAC GAG ACC CTG GGA GTC GTT GGA TCC ACC ACC ACT CAG CTG TAC ACG GAC CGC ACG       375
                135        REPEAT 1           145
    Glu Lys Leu Arg Pro Glu Met Glu Gly Pro Gly Ser Phe|Thr Ile Phe Ala Pro Ser Asn Glu Ala Trp Ala Ser
    GAG AAG CTG AGG CCT GAG ATG GAG GGT CCG GGC AGC TTC|ACC ATC TTC GCC CCT AGC AAC GAG GCC TGG GCC TCC       450
                        160                                      170
    Leu Pro Ala Glu Val Leu Asp Ser Leu Val Ser Asn Val Asn Ile Glu Leu Leu Asn Ala Leu Arg Tyr His Met
    TTG CCA GCT GAA GTG CTG GAC TCC CTG GTC AGC AAT GTC AAC ATT GAG CTG CTC AAT GCC CTC CGC TAC CAT ATG       525
```

Figure 5A

```
                                            185
Val Gly Arg Arg Val Leu Thr Asp Glu Leu Lys His Gly Met Thr Leu Thr Ser Met Tyr Gln Asn Ser Asn Ile
GTG GGC AGG CGA GTC CTG ACT GAT GAG CTG AAA CAC GGC ATG ACC CTC ACC TCT ATG TAC CAG AAT TCC AAC ATC   600

210
Gln Ile His His Tyr Pro Asn Gly Ile Val Thr Val Asn Cys Ala Arg Leu Leu Lys Ala Asp His His Ala Thr
CAG ATC CAC CAC TAT CCT AAT GGT ATA ACT GTA ACT GTG AAC TGT GCC CGG CTC CTG AAA GCC GAC CAC CAT GCA ACC   675

235
Asn Gly Val Val His Leu Ile Asp Lys Val Ile Ser Thr Ile Thr Asn Asn Ile Gln Gln Ile Ile Glu Ile Glu
AAC GGG GTG GTG CAC CTC ATC GAT AAG GTC ATC TCC ACC ATC ACC AAC AAC ATC CAG CAG ATT GAG ATC GAG   750

260                                      REPEAT 2
Asp Thr Phe Glu Thr Leu Arg Ala Ala Ala Val Ala Ala Ser Gly Leu Asn Thr Met Leu Glu Gly Asn Gly Gln Tyr
GAC ACC TTT GAG ACC CTT CGG GCT GCT GTG GCA TCA GGG CTC AAC ACG ATG CTT GAA GGT AAC GGC CAG TAC   825

285
Thr Leu Leu Ala Pro Thr Asn Glu Ala Phe Glu Lys Ile Pro Ser Glu Thr Leu Asn Arg Ile Leu Gly Asp Pro
ACG CTT TTG GCC CCG ACC AAT GAG GCC TTC GAG AAG ATC CCT AGT GAG ACT TTG AAC CGT ATC CTG GGC GAC CCA   900

310
Glu Ala Leu Arg Asp Leu Leu Asn Asn His Ile Leu Lys Ser Ala Met Cys Ala Ala Ile Ala Glu Val Ala Gly Leu
GAA GCC CTG AGA GAC CTG CTG AAC AAC CAC ATC TTG AAG TCA GCT ATG TGT GCT GAA GCC ATC GTT GCG GGG CTG   975

335
Ser Val Glu Thr Leu Glu Gly Thr Leu Glu Val Gly Cys Ser Gly Asp Met Leu Thr Ile Asn Gly Lys Ala
TCT GTA GAG ACC CTG GAG GGA ACA CTG GAG GTG GGC TGC AGC GGG GAC ATG CTC ACT ATC AAC GGG AAG GCG   1050

360
Ile Ile Ser Asn Lys Asp Ile Leu Ala Thr Asn Gly Val Ile His Tyr Ile Asp Glu Leu Leu Ile Pro Asp Ser
ATC ATC TCC AAT AAA GAC ATC CTA GCC ACC AAC GGG GTG ATC CAC TAC ATT GAT GAG CTA CTC ATC CCA GAC TCA   1125
```

Figure 5B

```
                                            385
Ala Lys Thr Leu Phe Glu Leu Ala Ala Glu Ser Asp Val Ser Thr Ala Ile Asp Leu Phe Arg Gln Ala Gly Leu
GCC AAG ACA CTA TTT GAA CTA GCT GCA GAG TCT GAT GTG TCC ACA GCC ATT GAC CTT TTC AGA CAA GCC GGC CTC   1200
              410 REPEAT 3
Gly Asn His Leu Ser Gly Ser Glu Arg Leu Thr Leu Ala Pro Leu Asn Ser Val Phe Lys Asp Gly Thr Pro
GGC AAT CAT CTC TCT GGA AGT GAG CGG TTG ACC CTG GCT CTG CCC CTG AAT TCT GTA TTC AAA GAT GGA ACC CCT   1275
                                    445
Pro Ile Asp Ala His Thr Arg Asn Leu Leu Arg Asn His Ile Ile Lys Asp Gln Leu Ala Ser Lys Tyr Leu Tyr
CCA ATT GAT GCC CAT ACA AGG AAT TTG CTT CGG AAC CAC ATA ATT AAA GAC CAG CTG GCC TCT AAG TAT CTG TAC   1350
                            470
His Gly Gln Thr Leu Glu Thr Leu Gly Gly Lys Lys Leu Arg Val Phe Val Tyr Arg Val Asn Ser Leu Cys Ile Glu
CAT GGA CAG ACC CTG GAA ACT CTG GGA GGC AAA AAA CTG AGA GTT TTT GTT TAT CGT AAT AGC CTC TGC ATT GAG   1425
                                            495
Asn Ser Cys Ile Ala Ala His Asp Lys Arg Gly Arg Tyr Gly Thr Leu Phe Thr Met Asp Arg Val Leu Thr Pro
AAC AGC TGC ATC GCG GCC CAC GAC AAG AGG GGG AGG TAC GGG ACC CTG TTC ACG ATG GAC CGG GTG CTG ACC CCC   1500
                                    520
Pro Met Gly Thr Val Met Asp Val Leu Lys Gly Asp Asn Arg Phe Ser Met Leu Val Ala Ala Ile Gln Ser Ala
CCA ATG GGG ACT GTC ATG GAT GTC CTG AAG GGA GAC AAT CGC TTT AGC ATG CTG GTA GCT GCC ATC CAG TCT GCA   1575
                    535 REPEAT 4
Gly Leu Thr Glu Thr Leu Asn Arg Glu Gly Gly Val Phe Val Tyr Thr Val Phe Ala Pro Thr Asn Glu Ala Phe Arg Ala Leu
GGA CTG ACG GAG ACC CTC AAC CGG GAA GGA GTC TAC ACA GTC TTT GCT CCC ACA AAT GAA GCC TTC CGA GCC CTG   1650
                                            570
Pro Pro Arg Glu Arg Ser Arg Leu Leu Gly Asp Ala Lys Glu Leu Leu Ala Asn Ile Leu Lys Tyr His Ile Gly Asp
CCA CCA AGA GAA CGG AGC AGG CTC TTG GGA GAT GCC AAG GAA CTT CTG GCC AAC ATC CTG AAA TAC CAC ATT GGT GAT   1725
```

Figure 5C

```
Glu Ile Leu Val Ser Gly Gly Ile Gly Ala Leu Arg Leu Val Arg Leu Lys Ser Leu Gln Gly Asp Lys Leu Glu Val Ser
GAA ATC CTG GTT AGC GGA GGC ATC GGG GCC CTG GTT CGG CTA GTG CGG CTA AAG TCT CTC CAA GGT GAC AAG CTG GAA GTC AGC      1800
                                                        585                                    595

Leu Lys Asn Asn Val Val Ser Val Asn Lys Glu Pro Val Ala Glu Pro Asp Ile Met Ala Thr Asn Gly Val Val
TTG AAA AAC AAT GTG GTG AGT GTC AAC AAG GAG CCT GTT GCC GAG CCT GAC ATC ATG GCC ACA AAT GGC GTG GTC      1875
                                        610

His Val Ile Thr Asn Val Leu Gln Pro Pro Ala Asn Arg Pro Gln Glu Arg Gly Asp Glu Leu Ala Asp Ser Ala
CAT GTC ATC ACC AAT GTT CTG CAG CCT CCA GCC AAC AGA CCT CAG GAA AGA GGG GAT GAA CTT GCA GAC TCT GCG      1960
                            635                                        645

Leu Glu Ile Phe Lys Gln Ala Ser Ala Phe Ser Arg Ala Ser Gln Arg Ser Val Arg Leu Ala Pro Val Tyr Gln
CTT GAG ATC TTC AAA CAA GCA TCA GCG TTT TCC AGG GCT TCC CAG AGG TCT GTG CGA CTA GCC CCT GTC TAT CAA      2025
                                660                                                670

Lys Leu Leu Glu Arg Met Lys His ***
AAG TTA TTA GAG AGG ATG AAG CAT TAGCTTGAAGCACTACACAGGAGAATGCACCACGGCTGTGGCCCCCAATTTCTCTCAGATTTCCACA      2116

GAGACTGTTTGAATGTTTCAAAACCAAGTATCACACTTTAATGTACATGGCCCGCACCACTGAATGACAATGAGCCTTGTGCATGGGGAGGAGGGA      2215

GAGAGATGTACTTTTTAAATCATGTTCCCCTAAACATGGCTGTTAACCACTGCAGAAACTTGGATGCAGAAACATTCACTCCTGACATTCACTTCCAGAGA      2314

GGACCTATCCAAATGTGGAATTGACTGCCAAGTCCCTATGCCAGAAAAGGAGCTTCAGTATTGTGGGCTCATAAAACATGAATCAGCAATCCAGC      2413

CTCATGGAAGCCTGGCACAGTTTTGTGAAAGCCCTTGCACACCTGAGAAATGGCATCATATTAAGCTATATGAGTTGAAATGTTCTGTCAAATGTGTC      2512

TCACAATCTACAGCTGGCTTGAGGCTTTTATGGGCCCCTGTCCCAGTAGAGCCTTAGATTTCCCTATTGTGACAGAGCCATG      2611

GTGTGTTTGTAATAATAAAACCAAAGAAACATA      2644
```

```
                                                                                           aa#
βIG-H3#1  NGVVHL IDKVI STITNNIQQIIEIEDTFEETLRAAVAAS GLNTM LEGNGQY.  275.
βIG-H3#2  NGVIHY IDHYI .....             LAAESDV STAIDLFRQAGLGNHLSG.SE RL     410.
βIG-H3#3  YGTLFT MDRVL TPPMGTV MDVLKGDNRFS MLVAAIQSAGLTE TLN REGVY.   537.
βIG-H3#4  NGVVHV ITNVL QPPANRP..QERGDELADSALEIFKQASAFSRASQRSV RL     670.
DrF-3     NGYVHI IDHVL GVPYTTV LGKLESDPMMSDTYKMGKFSHFNDQLNNTQRRF     503.
GrF-3     NGMVHI INKIL GVPYTTV KEKLRTDPMLNKTYHLGEMSDFNKMLDEKHTKF     510.
Mpb70     NATVYM IDSVL MPPA-COOH                                    193.
```

Fig. 6B

A549 Cells were Transfected and Plated as Described

A549 Cell +
pNEO +
Calf Thymus
DNA

A549 Cell +
pNEO +
pMT/H3

A549 Cell +
pNEO +
πH3M/H3

TGF-β INDUCED GENE

This application is a continuation-in-part U.S. patent application Ser. No. 07/833,835, filed Feb. 5, 1992, now abandoned.

TECHNICAL FIELD OF THE INVENTION

The present invention describes a novel TGF-β induced gene, βig-h3, and the protein encoded by this induced gene, βIG-H3, produced in response to TGF-β mediated growth inhibition of specific human cell lines.

BACKGROUND OF THE INVENTION

Transforming growth factor-β1 (TGF-β1) is a multifunctional regulator of cell growth and differentiation. It is capable of causing diverse effects such as inhibition of the growth of monkey kidney cells, (Tucker, R. F., G. D. Shipley, H. L. Moses & R. W. Holley (1984) Science 226:705-707) inhibition of growth of several human cancer cell lines, (Roberts, A. B., M. A. Anzano, L. M. Wakefiled, N. S. Roches, D. F. Stern & M. B. Sporn (1985) Proc. Natl. Acad. Sci. USA 82:119-123; Ranchalis, J. E., L. E. Gentry, Y. Agawa, S. M. Seyedin, J. McPherson, A. Purchio & D. R. Twardzik (1987) Biochem. Biophys. Res. Commun. 148:783-789) inhibition of mouse keratinocytes, (Coffey, R. J., N. J. Sipes, C. C. Bascum, R. Gravesdeal, C. Pennington, B. E. Weissman & H. L. Moses (1988) Cancer Res. 48:1596-1602; Reiss, M. & C. L. Dibble (1988 In Vitro Cell. Dev. Biol. 24:537-544) stimulation of growth of AKR-2B fibroblasts (Tucker, R. F., M. E. Olkenant, E. L. Branum & H. L. Moses (1988) Cancer Res. 43:1581-1586)and normal rat kidney fibroblasts, (Roberts, A. B., M. A. Anzano, L. C. Lamb, J. M. Smith & M. B. Sporn (1981) Proc. Natl. Acad. Sci. USA 78:5339-5343) stimulation of synthesis and secretion of fibronecfin and collagen, (Ignotz, R. A. & J. Massague (1986) J. Biol. Chem. 261:4337-4345; Centrella, M., T. L. McCarthy & E. Canalis (1987) J. Biol. Chem. 262:2869-2874) induction of cartilage-specific macromolecule production in muscle mesenchymal cells, (Seyedin, S. M., A. Y. Thompson, H. Bentz, D. M. Rosen, J. McPherson, A. Contin, N. R. Siegel, G. R. Galluppi & K. A. Piez (1986) J. Biol. Chem. 261:5693-5695) and growth inhibition of T and B lymphocytes. (Kehrl, J. H., L. M. Wakefiled, A. B. Roberts, S. Jakeoview, M. Alvarez-Mon, R. Derynck, M. B. Sporn & A. S. Fauci (1986) J. Exp. Med. 163:1037-1050; Kehrl, J. H., A. B. Roberts, L. M. Wakefield, S. Jakoview, M. B. Sporn & A. S. Fauci (1987) J. Immunol. 137:3855-3860; Kasid, A., G. I. Bell & E. P. Director (1988) J. Immunol. 141:690-698; Wahl, S. M., D. A. Hunt, H. L. Wong, S. Dougherty, N. McCartney-Francis, L. M. Wahl, L. Ellingsworth, J. A. Schmidt, G. Hall, A. B. Roberts & M. B. Sporn (1988) J. Immunol. 140:3026-3032)

Recent investigations have indicated that TGF-β1 is a member of a family of closely related growth-modulating proteins including TGF-β2, (Seyedin, S. M., P. R. Segarini, D. M. Rosen, A. Y. Thompson, H. Bentz & J. Graycar (1987) J. Biol. Chem. 262:1946-1949; Cheifetz, S., J. A. Weatherbee, M. L.-S. Tsang, J. K. Anderson, J. E. Mole, R. Lucas & J. Massague (1987) Cell 48:409-415; Ikeda, T., M. M. Lioubin & H. Marquardt (1987) Biochemistry 26:2406-2410) TGF-β1, (TenDijke, P., P. Hansen, K. Iwata, C. Pieler & J. G. Foulkes (1988) Proc. Natl. Acad. Sci. USA 85:4715-4719; Derynck, R., P. Lindquist, A. Lee, D. Wen, J. Tamm, J. L. Graycar, L Rhee, A. J. Mason, D. A. Miller, R. J. Coffey, H. L. Moses & E. Y. Chen (1988) EMBO J. 7:3737-3743; Jakowlew, S. B., P. J. Dillard, P. Kondaiah, M. B. Sporn & A. B. Roberts (1988) Mol. Endocrinology. 2:747-755) TGF-β4, (Jakowlew, S. B., P. J. Dillard, M. B. Sporn & A. B. Roberts (1988) Mol. Endocrinology. 2:1186-1195) Mullerian inhibitory substance, (Cate, R. L., R. J. Mattaliano, C. Hession, R. Tizard, N. M. Faber, A. Cheung, E. G. Ninfa, A. Z. Frey, D. J. Dash, E. P. Chow, R. A. Fisher, J. M. Bertonis, G. Torres, B. P. Wallner, K. L. Ramachandran, R. C. Ragin, T. F. Manganaro, D. T. Maclaughlin & P. K, Donahoe (1986) Cell 45:685-698) and the inhibins. (Mason, A. J., J. S. Hayflick, N. Ling, F. Esch, N. Ueno, S.-Y. Ying, R. Guillemin, H. Niall & P. H. Seeburg (1985) Nature 318:659-663)

TGF-β1 is a 24-kDa protein consisting of two identical disulfide-bonded 12 kD subunits. (Assoian, R. K., A. Komoriya, C. A. Meyers, D. M. Miller & M. B. Sporn (1983) J. Biol. Chem. 258:7155-7160; Frolik, C. A., L. L. Dart, C. A. Meyers, D. M. Miller & M. B. Sporn (1983) Proc. Natl. Acad. Sci. USA 80:3676-3680; Frolik, C. A., L. M. Wakefiled, D. M. Smith & M. B. Sporn (1984) J. Biol. Chem. 259:10995-11000) Analysis of cDNA clones coding for human, (Derynck, R., J. A. Jarrett, E. Y. Chem, D. H. Eaton, J. R. Bell, R. K. Assoian, A. B. Roberts, M. B. Sporn & D. V. Goeddel (1985) Nature 316:701-705) murine, (Derynck, R., J. A. Jarrett, E. Y. Chem, & D. V. Goeddel (1986) J. Biol. Chem. 261:4377-4379) and simian (Sharples, K., G. D. Plowman, T. M. Rose, D. R. Twardzik & A. F. Purchio (1987) DNA 6:239-244) TGF-β1 indicates that this protein is synthesized as a larger 390 amino acid pre-pro-TGF-β1 precursor; the carboxyl terminal 112 amino acid portion is then proteolyfically cleaved to yield the TGF-β1 monomer.

The simian TGF-β1 cDNA clone has been expressed to high levels in Chinese hamster ovary (CHO) cells. Analysis of the proteins secreted by these cells using site-specific antipeptide antibodies, peptide mapping, and protein sequencing revealed that both mature and precursor forms of TGF-β were produced and were held together, in part, by a complex array of disulfide bonds. (Gentry, L. E., N. R. Webb, J. Lim, A. M. Brunner, J. E. Ranchalis, D. R. Twardzik, M. N. Lioubin, H. Marquardt & A. F. Purchio (1987) Mol. Cell Biol. 7:3418-3427; Gentry, L. E., M. N. Lioubin, A. F. Purchio & H. Marquardt (1988) Mol. Cell. Biol. 8:4162-4168) Upon purification away from the 24kD mature rTGF-β1, the 90 to 110 kD precursor complex was found to consist of three species: pro-TGFβ1, the pro-region of the TGF-β1 precursor, and mature TGF-β1. (Gentry, L. E., N. R. Webb, J. Lim, A. M. Brunner, J. E. Ranchalis, D. R. Twardzik, M. N. Lioubin, H. Marquardt & A. F. Purchio (1987) Mol. Cell Biol. 7:3418-3427; Gentry, L. E., M. N. Lioubin, A. F. Purchio & H. Marquardt (1988) Mol. Cell. Biol. 8:4162-4168) Detection of optimal biological activity required acidification before analysis, indicating that rTGF-β1 was secreted in a latent form.

The pro-region of the TGF-β1 precursor was found to be glycosylated at three sites (Ash 82, Asn 136, and Asn 176) and the first two of these (Asn 82 and Ash 136) contain mannose-6-phosphate residues. (Brunner, A. M., L. E. Gentry, J. A. Cooper & A. F. Purchio (1988) Mol. Cell Biol. 8:2229-2232; Purchio, A. F., J. A. Cooper, A. M. Brunner, M. N. Lioubin, L. E. Gentry, K. S.

Kovacina, R. A. Roth & H. Marquardt (1988) J. Biol. Chem. 263:14211–14215) In addition, the rTGF-β1 precursor is capable of binding to the mannose-6-phosphate receptor and may imply a mechanism for delivery to lysomes where proteolytic processing can occur. (Kornfeld, S. (1986) J. Clin. Invest. 77: 1–6)

TGF-β2 is also a 24-kD homodimer of identical disulfide-bonded 112 amino acid subunits (Marquardt, H., M. N. Lioubin & T. Ikeda (1987) J. Biol. Chem. 262:12127–12131). Analysis of cDNA clones coding for human (Madisen, L., N. R. Webb, T. M. Rose, H. Marquardt, T. Ikeda, D. Twardzik, S. Seyedin & A. F. Purchio (1988) DNA 7:1–8; DeMartin, R., B. Plaendler, R. Hoefer-Warbinek, H. Gaugitsch, M. Wrann, H. Schlusener, J. M. Seifert, S. Bodmer, A. Fontana & E. Hoefer. EMBO J. 6:3673–3677) and simian (Hanks, S. K., R. Armour, J. H. Baldwin, F. Maldonado, J. Spiess & R. W. Holley (1988) Proc. Natl. Acad. Sci. USA 85:79–82) TGF-β2 showed that it, too, is synthesized as a larger precursor protein. The mature regions of TGF-β1 and TGF-β2 show 70% homology, whereas 30% homology occurs in the pro-region of the precursor. In the case of simian and human TGF-β2 precursor proteins differing by a 28 amino acid insertion in the pro-region; mRNA coding for these two proteins is thought to occur via differential splicing (Webb, N. R., L. Madisen, T. M. Rose & A. F. Purchio (1988) DNA 7:493–497).

The effects of TGF-β are thought to be mediated by the binding to specific receptors present on the surface of most cells (Massague, J. et at. (1985) J. Biol. Chem. 260:2636–2645; Segarini, P. R. et at. (1989) Mol. Endocrino. 3:261–272; Tucker, R. F., et at. (1984) Proc. Natl. Acad. Sci. USA 81:6757–6761; Wakefield, L. M., et at. (1987) J. Cell Biol. 105:965–975). Chemical crosslinking of [125I]-labeled TGF-β to cell surface components has identified three receptor size classes having molecule weights of 53–70 kDA (type I receptor), 80–120 kDa (type II receptor) and 250–350 kDa (type III receptor). The type I and II receptors have been implicated in signal transducfion (Boyd, F. T. et at. (1989) J. Biol. Chem. 264:2272–2278; Laiho, M., et al. (1990) J. Biol. Chem. 265:18518–18524) while the type III receptor has been suggested to act as a storage protein (Segarini, P. R. et al. (1989) Mol. Endocrino. 3:261–272). Little is known concerning signal transduction mechanisms which occur after receptor-ligand interaction.

The pleiotrophic effects of TGF-β may be due to its ability to affect the transcription of other genes. TGF-β has been shown to induce fos, myc and sis in AKR-2B cells (Leof, E. B., et al. (1986) Proc. Natl. Acad. Sci. USA 83:1453–1458):1453–1458) enhance expression of c-jun B in A549 cells (Pertovaara, L., et al. (1989) Molecular and Cellular Biology 9:1255–1264), increase the mRNA for matrix proteins (Penttinen, R. P., et al. (1988) Proc. Natl. Acad. Sci. USA 85:1105–1110), IL-6 (Elias, J. A., et al. (1991) J. Immunol. 146:3437–3446) and EGF-receptors (Thompson, K. L. et al. (1988) J. Biol. Chem. 263:19519–19528) and decrease expression of PDGF receptor α subunits (Battegay, E. J., et al. (1990) Cell 63:515–524). It alters the pattern of integrin expression in osteosarcoma cells (Heino, J., et al. (1989) J. Biol. Chem..264:21806–21813) and decreases the express of c-myc in keratinocytes (Coffey, R. J. et al. (1988b) Cancer Res. 48:1596–1602). TGF-β induces expression of Il-1β, TNF-α, PDGF and bFGF in human peripheral blood monocytes (McCartney-Francis, N., et at. (1991) DNA and Cell Biology 10:293–300).

SUMMARY OF THE INVENTION

The present invention is directed to a novel protein and gene induced by transforming growth factor beta (TGF-β) in mammalian cells.

In order to identify novel genes that encode protein products which might be involved in mediating some of the effects of TGF-β, a cDNA library was constructed from mRNA isolated from mammalian cells, such as human lung adenocarcinoma cells, which had been growth arrested by exposure to TGF-β. Several clones were isolated. One clone, termed TGF-β induced gene-h3 (βig-h3) encoded a novel protein, βIG-H3, containing 683 amino acid residues.

In the present invention a TGF-β induced protein is produced in growth arrested mammalian cells and preferably contains about 683 amino acid residues. The TGF-β induced protein preferably contains four homologous repeat regions of approximately 140 amino acids each and has an Arg-Gly-Asp sequence near its earboxy terminus. Treatment of mammalian cells such as human adenocarcinoma cells and embryonic mesenchymal cells with TGF-β produces a 10 to 20 fold increase in these cells of a 3.4 kb RNA construct that encodes a protein of this invention.

The present invention is further directed to the protein βIG-H3 which contains a 683 amino acid residue sequence corresponding to Sequence ID Number 2 and which contains an Arg-Gly-Asp at residues 642–644 of the amino acid sequence depicted in FIG. 5. βIG-H3 contains four homologous repeat regions that share at least 16% homology with each other.

A method for inhibiting the growth of tumor cells is contemplated by the present invention. The induction, expression and/or secretion of βIG-H3 has been shown to inhibit the growth, colony formation and appearance of tumor cells. In the method of the present invention, contacting tumor cells with βIG-H3 inhibits the growth of these cells.

The present invention is also directed to a nucleotide sequence that encodes a gene whose expression is strongly induced by TGF-β. The nucleotide sequence of the present invention can induce the production of a RNA transcript of about 3.4 kb, and preferably encodes the expression of βIG-H3.

DESCRIPTION OF THE FIGURES

In the drawings:

FIGS. 1A–D illustrate the expression βIG-H3 in A549 cells after treatment with TGF-β1 and TGF-β2. Confluent dishes of A549 cells grown in DMEM+10% FBS were split 1:10. Twenty hours later, they were treated with 20 ng/ml rTGF-β1 (A and C) or rTGF-β2 [D] for 72 hours. Total RNA was isolated and 25 μg was fractionated on an agarose-formaldehyde gel and analyzed by Northern blotting using [32P]-labeled βIG-H3 probe. Lane 1, RNA from untreated cells; lane 2, RNA from TGF-β treated cells. Exposure time for A and D, 10 hours; exposure time for C, 3 days. Panel B is a photograph of the gel in panel A stain with methylene blue. Bands were quantitated using a Molecular Dynamics Phosphoimager.

FIG. 2 illustrates the time course for induction of βIG-H3 mRNA by TGF-β1. Confluent dishes of A549 cells were split 1:10. Twenty hours later, they were treated with TGF-β1 (20 ng/ml) for 6 hours (lane 2), 24 hours (lane 3), 48 hours (lane 4), 72 hours (lane 5), or 96 hours (lane 6): RNA was isolated and hybridized to

[32-P]-labeled βig-h3 probe. Lane 1 contains RNA from untreated cells.

Figure 3:
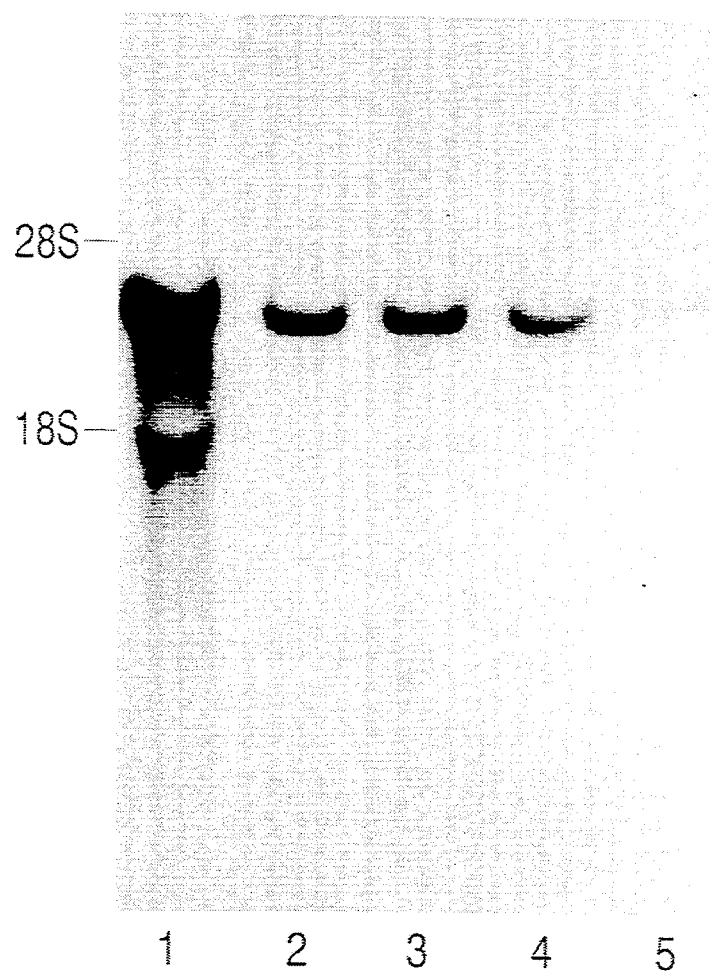

FIG. 3 illustrates the removal of TGF-β1 from the culture media of A549 cells leads to a decrease in synthesis of βig-h3 RNA. A549 cells were treated with TGF-β1 (20 ng/ml) for 3 days. Cells were then washed and grown in complete medium without TGF-β1 for 24 hours (lane 2), 48 hours (lane 3), 72 hours (lane 4) or 3 weeks (lane 5). RNA was extracted and analyzed by Northern blotting using [32-P]-labeled βig-h3 probe. Lane 1 contains RNA from A549 cells treated for 3 days with TGF-β1.

Figure 4:
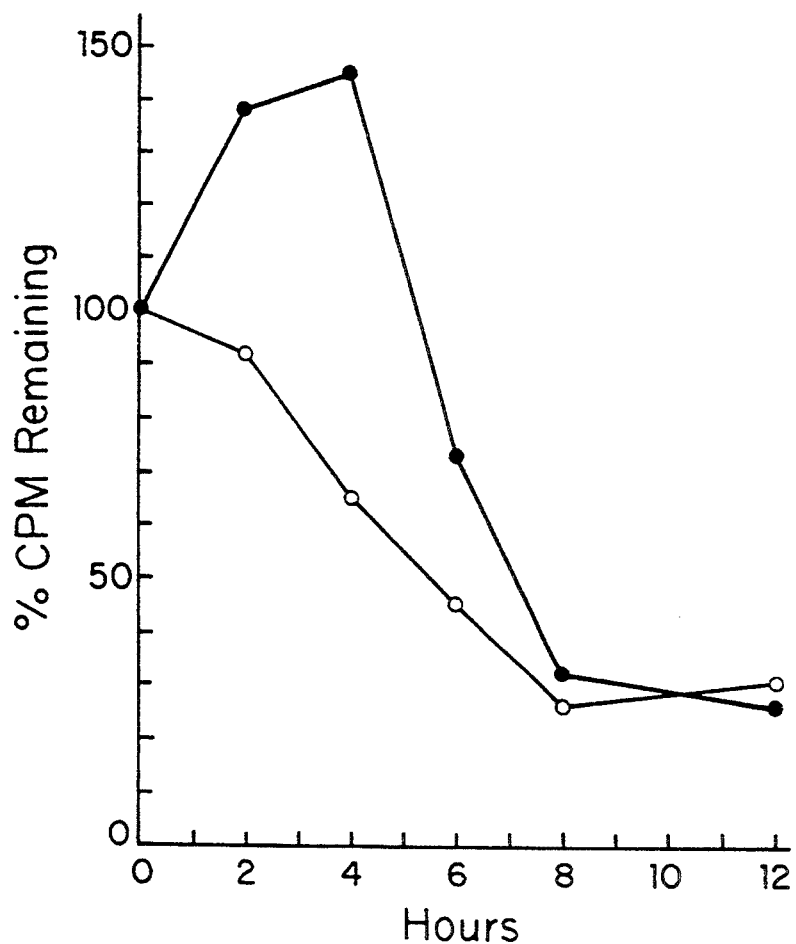

FIG. 4 illustrates the determination of βig-h3 mRNA half-life. A549 cells were treated with TGF-β (20 ng/ml) for 48 hours. Actinomycin D (10 ng/ml) was then added and RNA was extracted at the indicated times and analyzed by Northern blotting with [32-P]-labeled βig-h3 probe. Bands were quantitated using a Molecular Dynamics Phosphoimager and are plotted as percentage of cpm remaining in the 3.4 kb βig-h3 RNA band. O—O, untreated cells; ●—●, TGF-β treated cells.

FIG. 5 illustrates the nucleotide and deduced amino acid sequence of βIG-H3. Sequencing was performed as described (Sanger, F., et al. (1977) Proc. Natl. Acad. Sci. USA 74:5463–5467) and two dependent clones were sequenced for each region. The signal sequence is overlined and arrows mark predicted cleavage sites: the RGD sequence is boxed. Repeats 1 through 4 are bracketed and a polyadenylation signal at nucleotide 2625 is indicated (horizontal bracket).

Figure 6A:
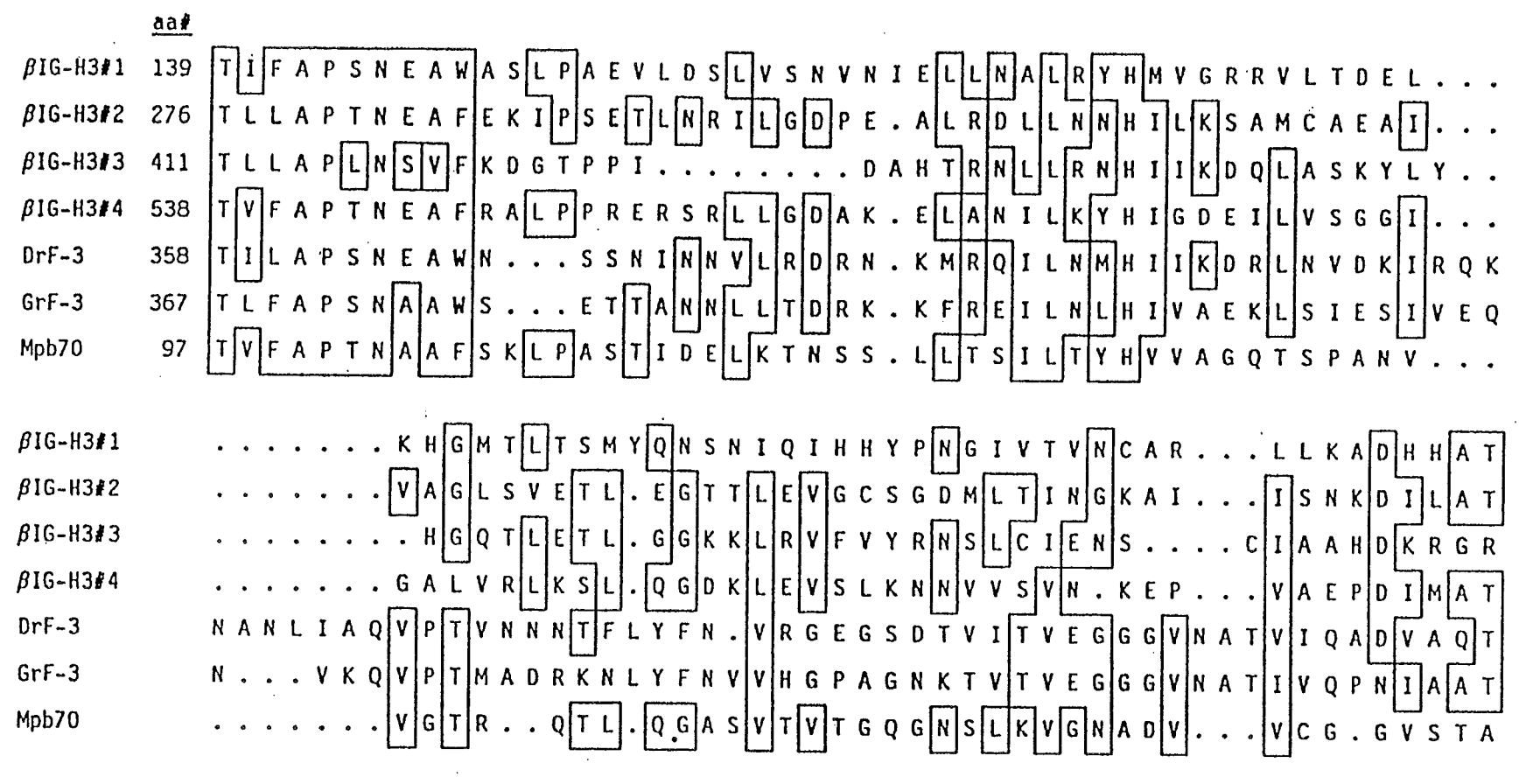

FIG. 6A illustrates the 4 homologous domains of βIG-H3 compared with the third repeats from drosophila fasciclin-I (DrF-3), grasshopper fasciclin-I (GrF-3), and the carboxy terminal half of the *Mycobacterium bovus* protein Mpb70. Boxed amino acids are identical to at least 2 others at that same position.

Figure 6B:
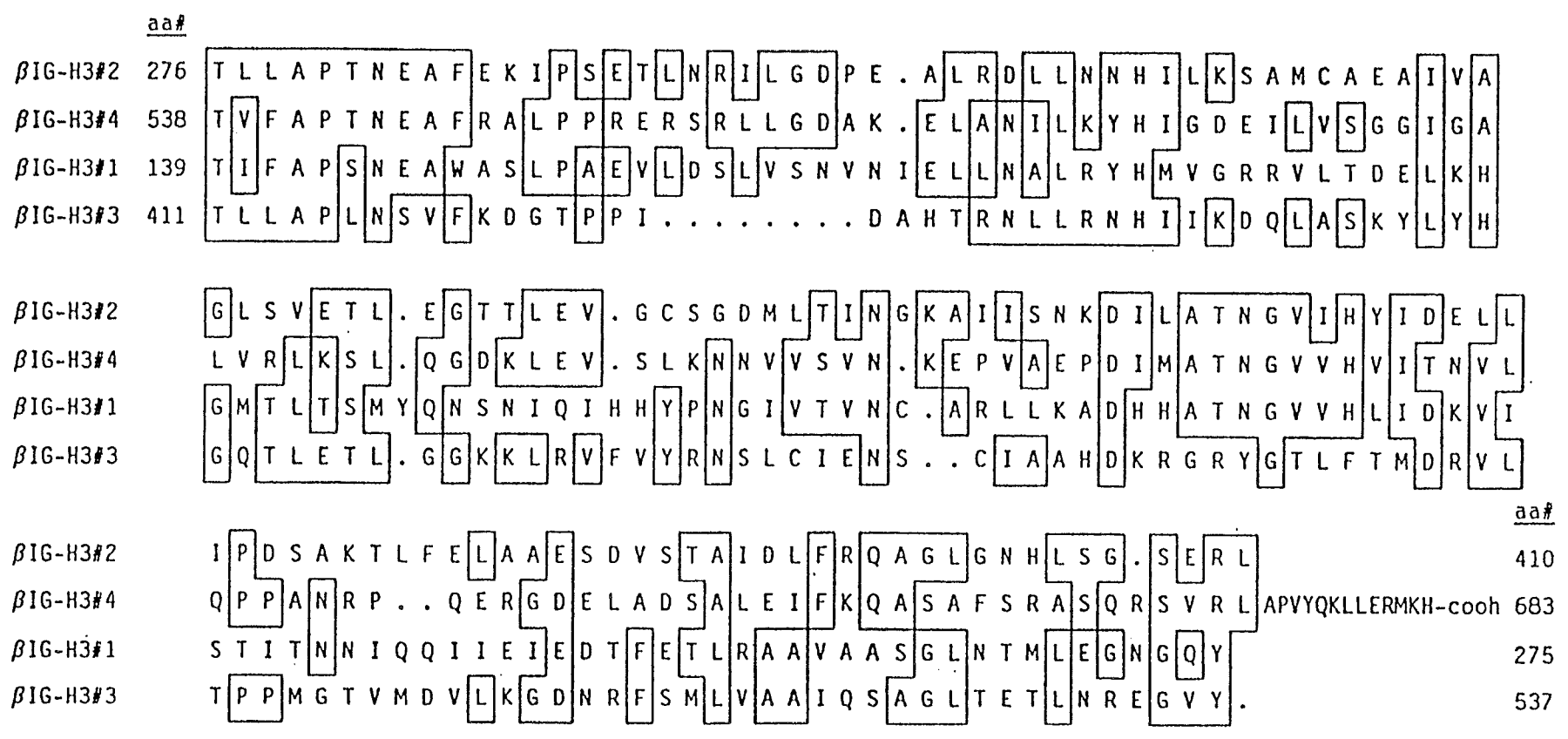

FIG. 6B illustrates the 4 repeats of βIG-H3 directly compared. Boxed amino acids are identical with at least 1 other at that same position. Multiple alignments were generated using the program Pileup of UW/GCG software.

Figure 7A:
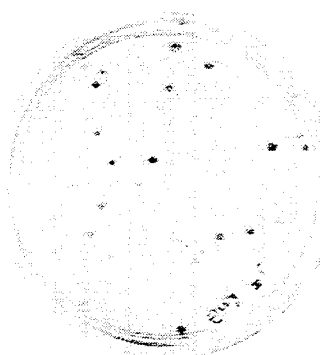
Figure 7B:
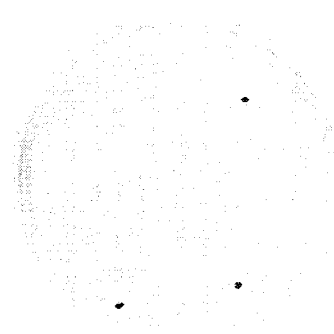
Figure 7C:
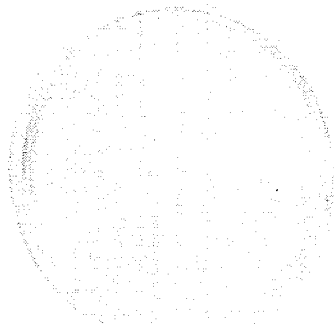

FIGS. 7A-C illustrate the inhibition of tumor cell colony formation produced by insertion of DNA encoding for βIG-H3. A549 tumor cells were transfected with βig-h3 DNA and the development of cell colonies were monitored. A549 cells transfected with a plasmid encoding the neomycin resistance gene (pNEO) and then divided into three groups that were additionally transfected, respectively, with A) calf thymus DNA (controls); or B) βig-h3 under the control of the metallothionine promoter (pMT/H3); or C) βig-h3 under the control of the CMV promoter (πH3M/H3).

DESCRIPTION OF PREFERRED EMBODIMENTS

The present invention is directed to a nucleotide sequence and a protein that is induced in mammalian cells in response to TGF-β.

The arrest of the growth of specific mammalian cells, such as human lung adenocarcinoma cells, by treatment with TGF-β resulted in the increased induction of a novel gene product. TGF-β refers to a family of highly-related dimeric proteins which are known to regulate the growth and differentiation of many cell type. As used herein, the term "TGF-β" refers to any member of the family of transforming growth factor beta which include TGF-β1, TGF-β2, TGF-β3, TGF-β4, TGF-β5 as well as the TGF-β1/β2 hybrid molecules, designated 5-β.

TGF-β is known to regulate the transcription of several genes, such as the genes encoding c-myc, c-sis, and the platelet-derived growth factor receptor. In the present invention, an attempt was made to identify novel genes whose protein products could be involved in mediating some of the pleiotropic effects of TGF-β. As a result of the present invention a new gene product has been identified in mammalian cells that have been growth arrested by TGF-β.

All amino acid residues identified herein are in the natural of L-configuration. In keeping with standard polypeptide nomenclature, abbreviations for amino acid residues are as follows:

| AMINO ACID | SYMBOL | |
|---|---|---|
| | 3-Letter | 1-Letter |
| Alanine | Ala | A |
| Arginine | Arg | R |
| Asparagine | Asn | N |
| Aspartic acid | Asp | D |
| Aspartic acid or Asparagine | Asx | B |
| Cysteine | Cys | C |
| Glutamine | Gln | Q |
| Glutamic acid | Glu | E |
| Glycine | Gly | G |
| Glutamic acid or Glutamine | Glx | Z |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In the present invention, a substantially pure protein is isolated. This protein is produced in a mammalian cell in response to contacting the cells with sufficient TGF-β to arrest the growth of the mammalian cell.

As used herein the term "mammalian cell" refers to cells derived from a mammal, or mammalian tumor, including human cells such as human lung adenocarcinoma cells, human embryonic palatal mesenchymal cells and human prostatic adenocarcinoma cells.

As used herein the term "induced" refers to the stimulation, promotion and/or amplification of transcription or translation in a target cell. In a preferred embodiment of the present invention either RNA or protein production can be induced by TGF-β in a mammalian cell.

In a particularly preferred embodiment, TGF-β induced protein of the present invention has an amino acid residue sequence of about 683 amino acid residues.

When mammalian cells, such as human lung adenocarcinoma are treated with TGF-β1, growth inhibition of the cells resulted. A cDNA library was constructed and screened in order to isolate a clone which displayed increased hybridization to a cDNA probe prepared from TGF-β1 treated cells. One clone was isolated and designated βig-h3.

It was found that TGF-β1 and TGF-β2 each induced βig-h3 in cells. The induction was reversible and resulted from an increase in transcription. Analysis of the induced βig-h3 DNA revealed an open reading frame that encoded a novel 683 amino acid protein, βIG-H3, which contained a secretory leader signal sequence and an Arg-Gly-Asp sequence. βIG-H3 contained four internal repeat regions. These repeat regions display limited homology with short regions of grasshopper and drosophila fasciclin-I and Mpb70 from mycobacterium bovus. Fasciclin-I is a surface recognition glycoprotein expressed on subsets of axon bundles in insect embryos. Fasciclin-I contains four homologous 150 amino acid domains and has approximately 40% homology between grasshopper and drosophila (Zimmet al. (1988) Cell 53:577–583). It is thus considered in this invention that βig-h3 may encode a novel surface recognition protein. As such, and as proposed for fasciclin-I, the four homologous repeats could suggest a tetrameric structure with two binding sites, one at each intrachain dimer. This structure allows one βIG-H3 molecule to bind to a surface protein on two different cells. Additionally, the Arg-Gly-Asp sequence in βIG-H3, which is not present in fasciclin-I, may allow for interactions with various integrins.

βIG-H3 represents a new gene product induced by TGF-β and may illumimate the pleiotropic effects of TGF-βas, partly, being due to its ability to regulate gene transcription. It has recently been shown that growth inhibition by TGF-βis linked to inhibition of phosphorylation of pRB, the product of the retinoblastoma susceptibility gene (Pietenpol, et al. (1990) Cell 61:777–75; Laiko et at. (1990) Cell 62:175–185). If βIG-H3 is involved in cell surface recognition, it may participate in cell-cell communication and in the transmission of intracellular signals that are involved in negative growth control.

The present invention is further described by the following Examples which are intended to be illustrative and not limiting.

EXAMPLE 1

Identification of βig-h3 and Induction By TGF-β

Several human cell lines were cultured and used in these studies. A549 and H2981 (both human lung adenocarcinoma) cells, and the human breast carcinoma cell lines (MDA 453, MDA468 and 293) were grown in Dulbecco's Modified Eagle's medium (DMEM) plus 10% fetal bovine serum FBS). The human breast carcinoma line MCF-7 was grown in DMEM+10% FBS containing 60 ng/ml of insulin, and human prostatic adenocarcinoma cells (PC-3) were grown in a mixture of DMEM and Hank's F-12 medium (1:1) containing 10% FBS. Several routine and general methological procedures were utilized and are described in the articles cited herein, all of which are incorporated by reference.

Confluent dishes of A549 cells were split 1:10. Twenty hours later, they were treated with 20 ng/ml recombinant TGF-β1 in complete medium for 72 hours. This resulted in an 80–90% inhibition of DNA synthesis. A549 cells which were not treated with TGF-β1 were used as controls. Poly (A) containing RNA was extracted and a cDNA library was constructed in λ gt-10 by the method described in Webb et al. (1987) DNA 6:71–78, which is incorporated herein by reference. Duplicate filters were screened with [$^{32}$-P]-labeled cDNA from treated and untreated cells. Plaques showing increased hybridization to the treated probe were purified through the tertiary stage and the cDNA inserts were subcloned into pEMBL, as described in Dente et al. (1983) Nucleic Acids Res. 11:1645–1654. Several clones were isolated and one clone, pβig-h3a, was chosen for further study.

DNA sequence analysis of pβig-h3 detects a major transcript of 3.4 kb which is induced about 10-fold in A549 cells after a 72 hours with TGF-β1 (FIG. 1A). A longer exposure of FIG. 1A demonstrates that the βig-h3 transcript can be detected at low levels in untreated cells (FIG. 1C) βig-h3 is also induced by TGF-β2, as shown in FIG. 1D, and thus appears to be a TGF-β induced gene. A time course induction is presented in FIG. 2 and indicated that maximal stimulation of βig-h3 by TGF-β1 in A549 cells occurred after 48 hours of TGF-β1 treatment (a 20-fold increase above untreated cells).

Noticeable morphological changes of A459 cells occur upon TGF-β treatment. The cells appear larger, more spread out and assume a flattened morphology. These phenotypic changes are reversed upon removal of TGF-β and regrowth of the cells in complete media.

Removal of TGF-β1 from the culture medium resulted in a decrease in the expression of βig-h3 to the levels found in untreated cells (FIG. 3) This finding is consistent with the reversible growth inhibition of those cells.

Total RNA was extracted from both untreated cells and from cells treated with TGF-β, as described above. The RNA was fractionated on a 1% agarose-formaldehyde gel, according to the method of Lehrach et al. (1977) Biochemistry 16:4743–4751, transferred to a nylon membrane (Hybond N, Amersham) and hybridized to [$^{32}$-P]-labeled probe, according to the method described in Madisen et at. (1988) DNA 7:1–8. The bands were quantitated using a Molecular Dynamics Phosphoimager.

Figure 2:
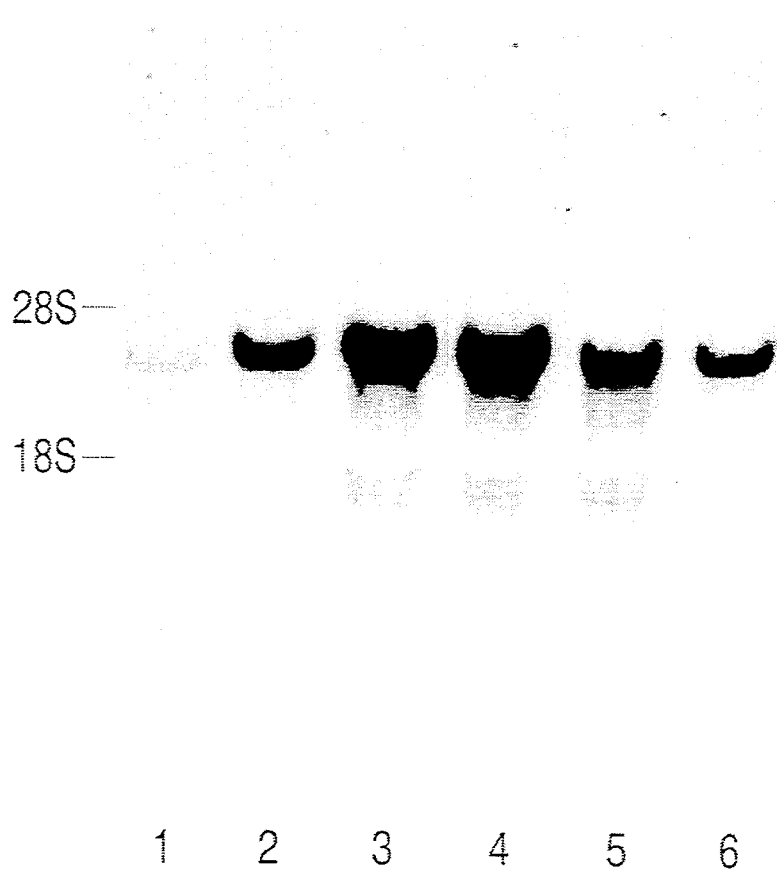

The increase in βig-h3 RNA could be due to either an increase in transcription or an increase in half-life. The half-life of the βig-h3 transcripts was determined in untreated and TGF-β1 treated A549 cells. The results shown in FIG. 4, illustrate that the half-life for βig-h3 RNA in untreated cells was about 5 hours, and is only slightly increased to 7 hours in TGF-β1 treated, transcriptionally inhibited (actinomycin D-treated) cells. The major increase in βig-h3 RNA thus appears to be due to an increase in transcription, rather than an increase in half-life. As shown in FIG. 2, the kinetics of βig-h3 message accumulation implies a half-life of 7–11 hours, which is the same range observed in the actinomycin D studies. This suggests that message stability is not grossly altered by actinomycin D in these studies.

Several human normal and cancer cell lines were examined for induction of βig-h3. TGF-β1 treatment of HEPM (human embryonic palatal mesenchymal) cells, H2981 cells resulted in an increase in βig-h3 mRNA. βig-h3 message was not induced by TGF-β1 in 293 cells nor in the breast cancer cell lines MCF-7, MDA453 or MDA468. The fact that βig-h3 is not induced in all cell types is not a unique finding, as the induction of other genes by TGF-β have been known to vary in different cell lines. For example, c-myc is reported to be stimulated in AKR-2B fibroblasts (Leof et at. (1986) Proc. Natl. Acad. Sci. USA 83:1453–1458), but down regulated in keratonicytes (Coffey et at. (1988) Cancer Res. 48:1596–1602).

EXAMPLE 2

Sequence Analysis

DNA sequence analysis was performed by the method of Sanger et at. (1977) Proc. Natl. Acad. Sci. USA 74:5463-54679.

Nucleotide sequence analysis of pβig-h3a revealed that it contained a partial open reading frame. The cDNA library was therefore rescreened with [$^{32}$-P]-labeled βig-h3a probe until several overlapping clones encoding the entire open reading frame were obtained. The nucleotide and deduced amino acid sequence of βIG-H3 is shown in FIG. 5 and is described in Sequence I.D. Number 1 and 2. The cDNA contains a single open reading frame encoding a 683 amino acid protein, βIG-H3. βIG-H3 contains an amino terminal signal peptide and an RGD sequence located at the carboxy terminus (residues 642-644). This motif has previously been shown to serve as a ligand recognition sequence for several integrins (Ruoslahti, E. (1989) J. Biol Chem. 264:13369-13371). There are no predicted sites of N-linked glycosylation. A polyadenylation signal is present at nucleotide residue 2624.

A Tfasta search of the Genebank and EMBL databases with the βig-h3 open reading frame indicated that the protein was unique. Short regions with homology to grasshopper and drosophila fasciclin-I and Mpb70 from *Mycobacterium bovus* were identified. FIG. 6/A shows multiple alignments of regions from these proteins.

Upon dot matrix analysis of βIG-H3 four homologous domains of approximately 140 amino acids were revealed. A comparison of these repeats is shown in FIG. 6B and illustrate interdomain homologies ranging from 31% (between domains 2 and 4) to 16% (between domains 1 and 3), with domain 3 the most divergent. These interdomain homologies are similar to those found in fasciclin-I, wherein repeat 2 appears to be the most divergent. The domains of βIG-H3 and fasciclin-I share 3 highly conserved amino acid stretches. One stretch contains 9 of 10 amino acids conserved at the amino end (T X F A P S N E A W). A second stretch has 6 of 8 amino acids conserved about 30 residues from the amino end (R X I L N X H I); and a third region near the carboxy end has 12 of 16 amino acids conserved (A T N G V V H X I D X V L X X P). These comparisons are illustrated in FIG. 6A.

Mpb70 in the major secreted protein from *Mycobacterium bovus*, the causal agent of bovine tuberculosis. Mpb70 occurs as a dimer of a 163 amino acid monomer with 33% homology to the βIG-H3 domains in the carboxy terminal 97 amino acids. The amino terminal 66 amino acids carry mycobacterium specific epitopes (Redford et al. (1990) J. of Gem Microbiol. 136:265-272).

EXAMPLE 3

Growth Inhibition of Cells By βIGH3

In order to study the ability of βIG-H3 to inhibit cell growth, transfection studies were carried out.

A549 tumors cells (American Type Culture Collection CCL 185) were transfected with the neomycin resistance gene (pNEO) under the control of the herpes simplex virus (HSV) promoter. The control cells were A549 cells transfected with pNEO and calf thymus DNA. The effect of βIG-H3 was studied by transfecting A549 cells with pNEO and βig-h3 under the control of either the metallothromine promoter (A549+-pNEO+MT/H3) or the cytomegalovirus promoter (A549+pNEO+πH3M/H3).

Approximately $5 \times 10^5$ cells were plated in 100 mm dishes in Dulbecco's Modified Eagle's Medium (DMEM, Gibco) supplemented with 10% fetal bovine serum (FBS) and maintained for 12 to 16 hours. The cells were then transfected using the DOTAP transfection reagent from Boehringer Mannheim. After approximately 24 hours cells were removed with trypsin in a total volume of 10 mi. Half of the harvested cells were then plated onto 100 ml dishes in DMEM+10% FBS containing 1 mg/ml of the antibiotic G-418 (Sigma) and maintained at 37° C. Approximately two to three weeks later the dishes were stained with crystal violet to indicate cell colonies that had formed and photographed. The results are shown in FIG. 7 which illustrates that cotransfection of cells with βIG-H3 encoding DNA resulted in a dramatic decrease in colony formation. This indicates that βIG-H3 may be a growth inhibitor induced by TGF-β.

Recombinant chinese hamster ovary cells (CHO) which secrete high levels of βIG-H3 were prepared and studied. Upon growth in culture, CHO cells secreting βIG-H3 appear bigger, flatter and grow more slowly than non-βIG-H3 secreting CHO cells. This suggests that the βIG-H3 protein may be inhibiting proliferation of these cells.

The foregoing description and Examples are intended as illustrative of the present invention, but not as limiting. Numerous variations and modifications may be effected without departing from the true spirit and scope of the present invention.

---

We claim:

1. An isolated nucleic acid sequence whose expression is induced by contacting cells which are A549 cells or H2981 cells with a TGFβ protein which is selected from the group consisting of TGFβ-1 and TGFβ-2, said nucleic acid sequence having SEQ ID #1.

2. The nucleic acid sequence of claim 1, wherein said TGFβ protein induces the production of a 3.4 kilobase RNA transcript from said nucleic acid sequence.

3. The nucleic acid sequence according to claim 1, wherein said nucleic acid sequence encodes the expression of βIG-H3 protein.

4. An isolated nucleic acid sequence which encodes βIG-H3 protein, said protein having SEQ ID #2, and whereto said protein is encoded by a nucleic acid sequence whose expression is reduced in cells which are A549 and H2981 cells with a TGFβ protein which is selected from the group consisting of TGFβ-1 or TGFβ-2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2691 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO -continued (vi) ORIGINAL SOURCE:
    (A) ORGANISM: Homo sapiens
    (F) TISSUE TYPE: LUNG
    (G) CELL TYPE: ADENOCARCINOMA
    (H) CELL LINE: A549

(xi) SEQUENCE DESCRIPTION: SEQ ID NO:1:

| | | | | | | |
|---|---|---|---|---|---|---|
| GCTTGCCCGT | CGGTCGCTAG | CTCGCTCGGT | GCGCGTCGTC | CCGCTCCATG | GCGCTCTTCG | 60 |
| TGCGGCTGCT | GGCTCTCGCC | CTGGCTCTGG | CCCTGGGCCC | CGCCGCGACC | CTGGCGGGTC | 120 |
| CCGCCAAGTC | GCCCTACCAG | CTGGTGCTGC | AGCACAGCAG | GCTCCGGGGC | CGCCAGCACG | 180 |
| GCCCCAACGT | GTGTGCTGTG | CAGAAGGTTA | TTGGCACTAA | TAGGAAGTAC | TTCACCAACT | 240 |
| GCAAGCAGTG | GTACCAAAGG | AAAATCTGTG | GCAAATCAAC | AGTCATCAGC | TACGAGTGCT | 300 |
| GTCCTGGATA | TGAAAAGGTC | CCTGGGGAGA | GGGCTGTCC | AGCAGCCCTA | CCACTCTCAA | 360 |
| ACCTTTACGA | GACCCTGGGA | GTCGTTGGAT | CCACCACCAC | TCAGCTGTAC | ACGGACCGCA | 420 |
| CGGAGAAGCT | GAGGCCTGAG | ATGGAGGGGC | CCGGCAGCTT | CACCATCTTC | GCCCCTAGCA | 480 |
| ACGAGGCCTG | GGCCTCCTTG | CCAGCTGAAG | TGCTGGACTC | CCTGGTCAGC | AATGTCAACA | 540 |
| TTGAGCTGCT | CAATGCCCTC | CGCTACCATA | TGGTGGGCAG | GCGAGTCCTG | ACTGATGAGC | 600 |
| TGAAACACGG | CATGACCCTC | ACCTCTATGT | ACCAGAATTC | CAACATCCAG | ATCCACCACT | 660 |
| ATCCTAATGG | GATTGTAACT | GTGAACTGTG | CCCGGCTCCT | GAAAGCCGAC | CACCATGCAA | 720 |
| CCAACGGGGT | GGTGCACCTC | ATCGATAAGG | TCATCTCCAC | CATCACCAAC | AACATCCAGC | 780 |
| AGATCATTGA | GATCGAGGAC | ACCTTTGAGA | CCCTTCGGGC | TGCTGTGGCT | GCATCAGGGC | 840 |
| TCAACACGAT | GCTTGAAGGT | AACGGCCAGT | ACACGCTTTT | GGCCCCGACC | AATGAGGCCT | 900 |
| TCGAGAAGAT | CCCTAGTGAG | ACTTTGAACC | GTATCCTGGG | CGACCCAGAA | GCCCTGAGAG | 960 |
| ACCTGCTGAA | CAACCACATC | TTGAAGTCAG | CTATGTGTGC | TGAAGCCATC | GTTGCGGGGC | 1020 |
| TGTCTGTAGA | GACCCTGGAG | GGCACGACAC | TGGAGGTGGG | CTGCAGCGGG | GACATGCTCA | 1080 |
| CTATCAACGG | GAAGGCGATC | ATCTCCAATA | AAGACATCCT | AGCCACCAAC | GGGGTGATCC | 1140 |
| ACTACATTGA | TGAGCTACTC | ATCCCAGACT | CAGCCAAGAC | ACTATTTGAA | TTGGCTGCAG | 1200 |
| AGTCTGATGT | GTCCACAGCC | ATTGACCTTT | TCAGACAAGC | CGGCCTCGGC | AATCATCTCT | 1260 |
| CTGGAAGTGA | GCGGTTGACC | CTCCTGGCTC | CCCTGAATTC | TGTATTCAAA | GATGGAACCC | 1320 |
| CTCCAATTGA | TGCCCATACA | AGGAATTTGC | TTCGGAACCA | CATAATTAAA | GACCAGCTGG | 1380 |
| CCTCTAAGTA | TCTGTACCAT | GGACAGACCC | TGGAAACTCT | GGGCGGCAAA | AAACTGAGAG | 1440 |
| TTTTTGTTTA | TCGTAATAGC | CTCTGCATTG | AGAACAGCTG | CATCGCGGCC | CACGACAAGA | 1500 |
| GGGGGAGGTA | CGGGACCCTG | TTCACGATGG | ACCGGGTGCT | GACCCCCCA | ATGGGACTG | 1560 |
| TCATGGATGT | CCTGAAGGGA | GACAATCGCT | TTAGCATGCT | GGTAGCTGCC | ATCCAGTCTG | 1620 |
| CAGGACTGAC | GGAGACCCTC | AACCGGGAAG | GAGTCTACAC | AGTCTTTGCT | CCCACAAATG | 1680 |
| AAGCCTTCCG | AGCCCTGCCA | CCAAGAGAAC | GGAGCAGACT | CTTGGGAGAT | GCCAAGGAAC | 1740 |
| TTGCCAACAT | CCTGAAATAC | CACATTGGTG | ATGAAATCCT | GGTTAGCGGA | GGCATCGGGG | 1800 |
| CCCTGGTGCG | GCTAAAGTCT | CTCCAAGGTG | ACAAGCTGGA | AGTCAGCTTG | AAAAACAATG | 1860 |
| TGGTGAGTGT | CAACAAGGAG | CCTGTTGCCG | AGCCTGACAT | CATGGCCACA | AATGGCGTGG | 1920 |
| TCCATGTCAT | CACCAATGTT | CTGCAGCCTC | CAGCCAACAG | ACCTCAGGAA | AGAGGGGATG | 1980 |
| AACTTGCAGA | CTCTGCGCTT | GAGATCTTCA | ACAAGCATC | AGCGTTTTCC | AGGGCTTCCC | 2040 |
| AGAGGTCTGT | GCGACTAGCC | CCTGTCTATC | AAAAGTTATT | AGAGAGGATG | AAGCATTAGC | 2100 |
| TTGAAGCACT | ACAGGAGGAA | TGCACCACGG | CAGCTCTCCG | CCAATTTCTC | TCAGATTTCC | 2160 |
| ACAGAGACTG | TTTGAATGTT | TTCAAAACCA | AGTATCACAC | TTTAATGTAC | ATGGGCCGCA | 2220 |

```
CCATAATGAG ATGTGAGCCT TGTGCATGTG GGGGAGGAGG GAGAGAGATG TACTTTTTAA      2280

ATCATGTTCC CCCTAAACAT GGCTGTTAAC CCACTGCATG CAGAAACTTG GATGTCACTG      2340

CCTGACATTC ACTTCCAGAG AGGACCTATC CCAAATGTGG AATTGACTGC CTATGCCAAG      2400

TCCCTGGAAA AGGAGCTTCA GTATTGTGGG GCTCATAAAA CATGAATCAA GCAATCCAGC      2460

CTCATGGGAA GTCCTGGCAC AGTTTTTGTA AAGCCCTTGC ACAGCTGGAG AAATGGCATC      2520

ATTATAAGCT ATGAGTTGAA ATGTTCTGTC AAATGTGTCT CACATCTACA CGTGGCTTGG      2580

AGGCTTTTAT GGGGCCCTGT CCAGGTAGAA AAGAAATGGT ATGTAGAGCT TAGATTTCCC      2640

TATTGTGACA GAGCCATGGT GTGTTTGTAA TAATAAAACC AAAGAAACAT A              2691
```

( 2 ) INFORMATION FOR SEQ ID NO:2:

( i ) SEQUENCE CHARACTERISTICS:
        ( A ) LENGTH: 683 amino acids
        ( B ) TYPE: amino acid
        ( D ) TOPOLOGY: linear ( i i ) MOLECULE TYPE: protein ( i i i ) HYPOTHETICAL: YES ( v ) FRAGMENT TYPE: internal ( v i ) ORIGINAL SOURCE:
        ( A ) ORGANISM: Homo sapiens
        ( F ) TISSUE TYPE: LUNG
        ( G ) CELL TYPE: ADENOCARCINOMA
        ( H ) CELL LINE: A549

( x i ) SEQUENCE DESCRIPTION: SEQ ID NO:2:

```
Met Ala Leu Phe Val Arg Leu Leu Ala Leu Ala Leu Ala Leu Ala Leu
  1               5                  10                  15

Gly Pro Ala Ala Thr Leu Ala Gly Pro Ala Lys Ser Pro Tyr Gln Leu
             20                  25                  30

Val Leu Gln His Ser Arg Leu Arg Gly Arg Gln His Gly Pro Asn Val
         35                  40                  45

Cys Ala Val Gln Lys Val Ile Gly Thr Asn Arg Lys Tyr Phe Thr Asn
 50                  55                  60

Cys Lys Gln Trp Tyr Gln Arg Lys Ile Cys Gly Lys Ser Thr Val Ile
 65                  70                  75                  80

Ser Tyr Glu Cys Cys Pro Gly Tyr Glu Lys Val Pro Gly Glu Lys Gly
                 85                  90                  95

Cys Pro Ala Ala Leu Pro Leu Ser Asn Leu Tyr Glu Thr Leu Gly Val
            100                 105                 110

Val Gly Ser Thr Thr Thr Gln Leu Tyr Thr Asp Arg Thr Glu Lys Leu
        115                 120                 125

Arg Pro Glu Met Glu Gly Pro Gly Ser Phe Thr Ile Phe Ala Pro Ser
    130                 135                 140

Asn Glu Ala Trp Ala Ser Leu Pro Ala Glu Val Leu Asp Ser Leu Val
145                 150                 155                 160

Ser Asn Val Asn Ile Glu Leu Leu Asn Ala Leu Arg Tyr His Met Val
                165                 170                 175

Gly Arg Arg Val Leu Thr Asp Glu Leu Lys His Gly Met Thr Leu Thr
            180                 185                 190

Ser Met Tyr Gln Asn Ser Asn Ile Gln Ile His His Tyr Pro Asn Gly
        195                 200                 205

Ile Val Thr Val Asn Cys Ala Arg Leu Leu Lys Ala Asp His His Ala
    210                 215                 220

Thr Asn Gly Val Val His Leu Ile Asp Lys Val Ile Ser Thr Ile Thr
225                 230                 235                 240
```

-continued

```
Asn  Asn  Ile  Gln  Gln  Ile  Ile  Glu  Ile  Glu  Asp  Thr  Phe  Glu  Thr  Leu
               245                250                     255

Arg  Ala  Ala  Val  Ala  Ala  Ser  Gly  Leu  Asn  Thr  Met  Leu  Glu  Gly  Asn
          260                 265                     270

Gly  Gln  Tyr  Thr  Leu  Leu  Ala  Pro  Thr  Asn  Glu  Ala  Phe  Glu  Lys  Ile
          275                 280                     285

Pro  Ser  Glu  Thr  Leu  Asn  Arg  Ile  Leu  Gly  Asp  Pro  Glu  Ala  Leu  Arg
     290                      295                300

Asp  Leu  Leu  Asn  Asn  His  Ile  Leu  Lys  Ser  Ala  Met  Cys  Ala  Glu  Ala
305                      310                315                          320

Ile  Val  Ala  Gly  Leu  Ser  Val  Glu  Thr  Leu  Glu  Gly  Thr  Thr  Leu  Glu
               325                 330                               335

Val  Gly  Cys  Ser  Gly  Asp  Met  Leu  Thr  Ile  Asn  Gly  Lys  Ala  Ile  Ile
               340                 345                     350

Ser  Asn  Lys  Asp  Ile  Leu  Ala  Thr  Asn  Gly  Val  Ile  His  Tyr  Ile  Asp
          355                 360                     365

Glu  Leu  Leu  Ile  Pro  Asp  Ser  Ala  Lys  Thr  Leu  Phe  Glu  Leu  Ala  Ala
     370                 375                      380

Glu  Ser  Asp  Val  Ser  Thr  Ala  Ile  Asp  Leu  Phe  Arg  Gln  Ala  Gly  Leu
385                 390                      395                          400

Gly  Asn  His  Leu  Ser  Gly  Ser  Glu  Arg  Leu  Thr  Leu  Leu  Ala  Pro  Leu
               405                      410                     415

Asn  Ser  Val  Phe  Lys  Asp  Gly  Thr  Pro  Pro  Ile  Asp  Ala  His  Thr  Arg
               420                 425                     430

Asn  Leu  Leu  Arg  Asn  His  Ile  Ile  Lys  Asp  Gln  Leu  Ala  Ser  Lys  Tyr
          435                 440                      445

Leu  Tyr  His  Gly  Gln  Thr  Leu  Glu  Thr  Leu  Gly  Gly  Lys  Lys  Leu  Arg
     450                      455                460

Val  Phe  Val  Tyr  Arg  Asn  Ser  Leu  Cys  Ile  Glu  Asn  Ser  Cys  Ile  Ala
465                      470                 475                          480

Ala  His  Asp  Lys  Arg  Gly  Arg  Tyr  Gly  Thr  Leu  Phe  Thr  Met  Asp  Arg
               485                 490                               495

Val  Leu  Thr  Pro  Pro  Met  Gly  Thr  Val  Met  Asp  Val  Leu  Lys  Gly  Asp
               500                 505                     510

Asn  Arg  Phe  Ser  Met  Leu  Val  Ala  Ala  Ile  Gln  Ser  Ala  Gly  Leu  Thr
          515                 520                      525

Glu  Thr  Leu  Asn  Arg  Glu  Gly  Val  Tyr  Thr  Val  Phe  Ala  Pro  Thr  Asn
     530                      535                540

Glu  Ala  Phe  Arg  Ala  Leu  Pro  Pro  Arg  Glu  Arg  Ser  Arg  Leu  Leu  Gly
545                      550                      555                     560

Asp  Ala  Lys  Glu  Leu  Ala  Asn  Ile  Leu  Lys  Tyr  His  Ile  Gly  Asp  Glu
               565                 570                     575

Ile  Leu  Val  Ser  Gly  Gly  Ile  Gly  Ala  Leu  Val  Arg  Leu  Lys  Ser  Leu
               580                 585                     590

Gln  Gly  Asp  Lys  Leu  Glu  Val  Ser  Leu  Lys  Asn  Asn  Val  Val  Ser  Val
          595                 600                      605

Asn  Lys  Glu  Pro  Val  Ala  Glu  Pro  Asp  Ile  Met  Ala  Thr  Asn  Gly  Val
     610                 615                      620

Val  His  Val  Ile  Thr  Asn  Val  Leu  Gln  Pro  Pro  Ala  Asn  Arg  Pro  Gln
625                      630                      635                     640

Glu  Arg  Gly  Asp  Glu  Leu  Ala  Asp  Ser  Ala  Leu  Glu  Ile  Phe  Lys  Gln
               645                      650                     655

Ala  Ser  Ala  Phe  Ser  Arg  Ala  Ser  Gln  Arg  Ser  Val  Arg  Leu  Ala  Pro
               660                 665                      670
```

-continued

```
Val  Tyr  Gln  Lys  Leu  Leu  Glu  Arg  Met  Lys  His
          675                 680
```